United States Patent [19]
Jatteau et al.

[11] Patent Number: 5,428,223
[45] Date of Patent: Jun. 27, 1995

[54] MINICAMERA FOR PROXIMITY DETECTION OF NUCLEAR RADIATION EMITTED BY A RADIOISOTOPE, AND ITS APPLICATION AS A SURGICAL TOOL

[75] Inventors: Michel Jatteau; Pierre Klein, both of Paris, France

[73] Assignee: U.S. Philips Corporation, New York, N.Y.

[21] Appl. No.: 232,924

[22] Filed: Apr. 25, 1994

[30] Foreign Application Priority Data

Apr. 28, 1993 [FR] France .................. 93 05000

[51] Int. Cl.$^6$ .................................................. G01T 1/20
[52] U.S. Cl. .................... 250/363.06; 250/363.09; 250/362
[58] Field of Search ............... 250/363.06, 363.09, 250/363.1, 363.02, 370.06, 362

[56] References Cited

U.S. PATENT DOCUMENTS 3,940,626  2/1976  Hounsfield ............... 250/366
4,595,014  6/1986  Barrett et al. ........... 250/363.06

FOREIGN PATENT DOCUMENTS 2725859  3/1979  Germany ............... 250/363.96

*Primary Examiner*—Paul M. Dzierzynski
*Assistant Examiner*—Richard Hanig
*Attorney, Agent, or Firm*—Jack D. Slobod

[57] ABSTRACT

A minicamera detects at least one $\beta$ and $\gamma$ nuclear radiation (or assimilated) emitted by a radioisotope present in a body (1, 2). Its image pick-up head (300) includes a collimator (301), a scintillator (302) and a photodetector assembly (303 to 309). In accordance with the invention, the image pick-up head (300) also includes a modulating grid (312) with holes which is arranged between the collimator (301) and the scintillator (302). The grid can completely open or close the collimator under the influence of a suitable mechanism (313). The signals acquired by the photodetector assembly in the open position are applied to a first image memory (423) whereas those acquired in the closed position are applied to a second image memory (424). Comparison and calculation means (421) provide the desired useful signal by simple subtraction of the contents of the two memories (423, 424).

11 Claims, 2 Drawing Sheets

MINICAMERA FOR PROXIMITY DETECTION OF NUCLEAR RADIATION EMITTED BY A RADIOISOTOPE, AND ITS APPLICATION AS A SURGICAL TOOL

BACKGROUND OF THE INVENTION

1. Field of the Invention

The invention relates to a minicamera for the detection of at least a composite $\beta$ and $\gamma$ nuclear radiation, or a $\gamma$ nuclear radiation associated with conversion electrons assimilated with a $\beta$ radiation, emitted by a radioisotope present in a body, its image pick-up head comprising a $\beta$ radiation collimator which is transparent to the $\gamma$ radiation, a scintillator and a photodetector assembly.

It is preferably used for the detection of a composite $\beta$ and $\gamma$ radiation emitted by a tracer radioisotope already assimilated by an organism, in which case it is intended to be applied against the incision made in said organism in the course of a surgical operation; the image pick-up head is then provided with a protective diaphragm. In this case it concerns a surgical camera.

2. Description of the Related Art

Specialist technical literature describes minicameras which form an image of molecules marked by pure $\beta$ emitters (molecular biology) or which detect the presence of $\beta$ radiation (beam study, impact research in particle physics).

The role of tracers has become of prime importance in medicine. It is notably possible to mark cancerous tumors by means of the radioisotope $^{131}I$ which belongs to the family of markers emitting $\beta$ and $\gamma$ simultaneously. The $\beta$ radiation emitted by $^{131}I$ has the property that it has a very limited interaction mean free path within the tissues, i.e. of the order of from 1 to 2 mm, considering its mean energy of a few hundreds of keV. The idea underlying the invention is the aim to detect this $\beta$ radiation emitted by a marked cancerous tissue, which is possible only during a surgical operation consisting of the excision of the cancerous tumor, in the absence of which the presence of healthy tissues covering the cancerous tissues would prevent any detection of this $\beta$ radiation inevitably absorbed by these healthy tissues. The exact technical problem to be solved at this stage is the elimination of the $\gamma$ radiation which accompanies the $\beta$ radiation and whose resultant detection signal has an amplitude which is substantially higher than that of the $\beta$ radiation.

SUMMARY OF THE INVENTION

In accordance with the invention, this problem is solved in that the minicamera of the kind set forth is characterized in that said image pick-up head also comprises a modulating grid with holes which is arranged between the collimator and the scintillator so as to be movable by a mechanism so that in an alternating fashion it opens the holes of the collimator in a first position and closes these holes in a second position, said photodetector assembly being controlled so as to integrate the alternating signals supplied by the scintillator in said first position and said second position of the modulating grid and to apply these signals selectively to a first, open-grid image memory and to a second, closed-grid image memory, said minicamera also comprising means for calculation and comparison of signals stored in said first and second image memories in order to supply the useful signal to be displayed. Preferably, the minicamera also comprises an external protective diaphragm for the image pick-up head.

It is to be noted that U.S. Pat. No. 3,940,626 discloses a camera which is sensitive to $\gamma$ radiation and which comprises a modulating grid. However, this grid serves to enable a downstream photomultiplier tube to supply output signals which can be used to mark the scintillator excited by a $\gamma$ photon from among the p scintillators optically coupled to the photocathode of this photomultiplier. Actually, this modulating grid comprises two obturators which are displaced in synchronism, one being a light obturator arranged between the scintillator and the photomultiplier whereas the other is an obturator for the incident $\gamma$ radiation.

Referring to the present invention again, concerning composite $\gamma$ and $\beta$ radiation emitted by a marked cancerous tumor, a preferred embodiment of the minicamera is characterized in that the collimator, intended for the $\gamma$ radiation, is transparent to the $\gamma$ radiation, the solid part of said modulating grid being transparent to the $\gamma$ radiation but opaque to the $\beta$ radiation, and that said means for calculation and comparison are conceived so as to weight the signals of the first and the second memory in order to achieve equal signal integration times for correction of the bias introduced on the $\gamma$ signal by the changing of the position of the grid, and subsequently to take as the useful signal to be displayed the difference between the contents of homologous pixels, weighted and corrected for their bias, of the first image memory and the second image memory.

This technique can also be applied as such to the $\gamma$ emitters which present numerous conversion electrons associated with the $\gamma$ transition (transitions). The conversion electrons can then be assimilated with a $\beta$ radiation.

The modulating grid being made of a material which is transparent to the $\gamma$ radiation, the same quantity of $\gamma$ radiation (except for a small bias) is detected with an open grid and an obturating grid, provided that the detection times are equal. However, the $\beta$ radiation (simultaneous with $\gamma$) is detected with an open grid but not with an obturating grid. The difference between the two detections thus eliminates the $\gamma$ radiation, considered to be parasitic, even if it constitutes 95% of the energy detected, and reveals the $\gamma$ radiation emitted during half the duration of operation. More generally speaking, as it is desirable to detect preferably the $\gamma$ radiation emitted in order to obtain an image of the tissues to be excised more quickly, the time during which the grid is open relative to the time during which the grid is closed can be increased by a given ratio, after which the radiation detected can be weighted by multiplication inversely proportionally to the time ratio before execution of the subtraction aiming to eliminate the $\gamma$ signal. It is to be noted that such a subtraction offers the advantage that the major part of the noise is eliminated by subtraction between two noises which are closely correlated because they are very close in time. This enables notably alleviation of the cooling requirements to be imposed on the charge transfer detector matrix forming part of the photodetector assembly.

In the course of the exeresis, the surgeon can thus bring the image pick-up head of the minicamera close to the wound, preferably even in contact with the latter, in order to obtain a better image definition by collimation and to know exactly the part of the tumor still to be removed during the operation, the aim being the complete removal of exclusively the tumor.

A preferred embodiment of the invention which is compatible with the foregoing embodiments is characterized in that, said radiation being emitted by $^{131}$I, the minicamera comprises an external protective diaphragm which is made of metallized Kapton or vinyl, is opaque to visible radiation, and has a thickness of some tens of microns, a collimator which comprises parallel holes with a diameter of 1 mm and a pitch of 1.5 mm, is made of aluminium or brass, and has a thickness of from some tenths of a mm to a few mm, a modulating grid which is made of aluminium, copper or brass, has a thickness of some tenths of a ram, and is pierced like said modulator, and a scintillator which is formed by a sheet of a plastics material of the type NE 102 or 108, has a thickness of between 0.5 and 1.5 mm, and covers the field of view of the order of a few cm$^2$.

BRIEF DESCRIPTION OF THE DRAWING

The invention will be described in detail hereinafter with (reference to the accompanying drawing, wherein.

DETAILED DESCRIPTION OF THE PREFERRED EMBODIMENTS

Figure 1:
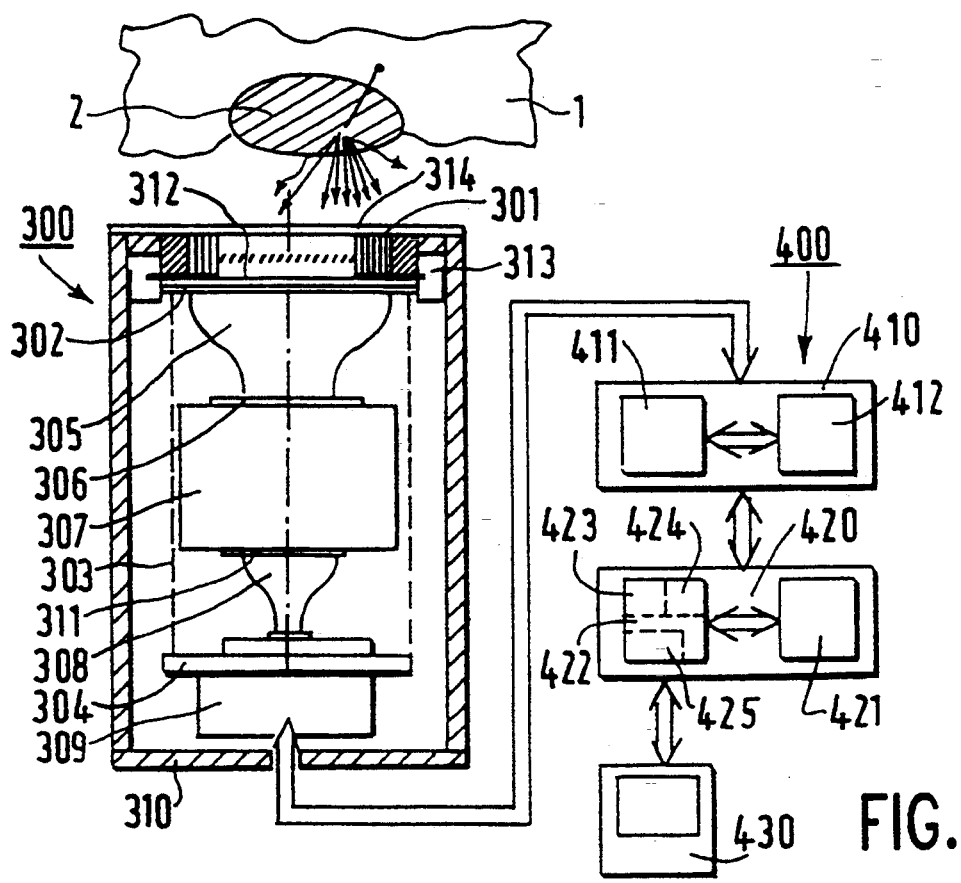
FIG. 1 shows a minicamera in accordance with the invention, the image pick-head being shown in a cross-sectional view.

The minicamera shown in FIG. 1 is designed to detect nuclear radiation, either composite $\beta$ and $\gamma$ radiation or pure $\gamma$ radiation, emitted by a body 1 which includes a region 2 which is marked by a tracer. The minicamera is formed by an image pick-up head 300 and an electronic imaging section 400.

As is known notably for a $\gamma$ camera, the image pick-up head comprises a collimator with parallel holes 301 which provides the desired angle of aperture in the intended direction, and a scintillator 302 in which the nuclear radiation interacts so as to produce photons in the visible domain. The visible photons are subsequently captured by a photodetector assembly 303 which implements, in a conventional manner, the optical coupling and adequate intensification of light between the output face of the scintillator 302 and the entrance window of a charge transfer detector matrix 304. A preferred embodiment of the photodetector assembly comprises a first fibre-optical beam reducer 305 which couples the scintillator 302 to the photocathode 306 of a light intensifier tube 307, for example of the Philips series XX 1410, whereas a second fibre-optical beam reducer 308 couples the exit screen 311 of the light intensifier tube 307 to the matrix 304 for the transfer of frames, for example of the Philips and Valvo type NXA 1011. The part denoted by the reference 309 is an image read-out device. A casing 310 on the one hand allows for mounting of the various components of the image pick-up head and on the other hand offers protection against ambient $\gamma$ radiation.

The electronic imaging assembly 400 consists in known manner of an electronic control and interface unit 410, an imaging sub-assembly 420 and a colour television monitor 430.

In an embodiment of the invention, the unit 410 accommodates the circuits 411 providing the power supply functions for the image pick-up head and other electronic circuits, and the circuits 412 which realise the functions of video amplification, sequencing of image reading, and interfacing with a processor 421 which comprises the customary peripherals and forms part of an imaging sub-assembly 420 which also comprises memories, notably memories for storage of the digital contents of pixels constituting the useful signal to be displayed. These memories relate to interfacing and image processing video cards 422 of the type VGF or AFG (manufactured by Imaging Technology, USA).

On the colour television monitor 430 the ultimate images (after digital processing) are displayed For the user.

In accordance with the invention, the known structure described above is extended with a modulating grid 312 with holes which is arranged between the collimator 301 and the scintillator 302. This grid is pierced in the same way as the collimator 301. It is displaceable and preferably describes a reciprocating rectilinear translatory motion under the control of a mechanism for alternately opening, in a first position, and obturating closing, in a second position, the holes of the collimator with a very low frequency which is typically 1 Hz. Thus, the image pick-up head can detect two types of nuclear radial:ion, i.e. either the nuclear radiation emitted by the part 2 which strikes the scintillator after having passed through the holes of the collimator and the grid, or the nuclear radiation filtered through the solid part of the grid. This results in two types of signals integrated by the matrix 304. The read operation, in 309, is performed in synchronism with the mechanism for the alternating displacement of the grid so that the signals read from the matrix are stored, in the form of digital images, selectively in a first, open-grid memory 423 and a second, obturating-grid memory 424, respectively.

The mechanism for displacing the modulating grid 312 is realised, for example by means of an electromagnet or electromagnets symbolized by the reference 313 in FIG. 1. Details concerning the mechanical aspects of the invention will be given hereinafter with reference to FIG. 3. In a first preferred embodiment of the invention, the minicamera is conceived to detect a composite $\beta$ and $\gamma$ nuclear radiation emitted by a tracer radioisotope (for example, iodine $^{131}$I) already assimilated by an organism, the camera being intended to be applied against the incision made in said organism in the course of a surgical operation. In order to protect the apparatus against the blood and the parasitic luminous radiation from the operating room, a protective diaphragm 314, for example of metallized Kapton or vinyl, is provided on the image pick-up head, which diaphragm is opaque to the visible radiation and has a thickness of some tens of microns.

The aim is to enable the formation of images of $\beta$ radiation emitted by the marked region 2 in the presence of intense $\gamma$ radiation. To this end, collimation is performed by a $\beta$ radiation collimator 301 which comprises parallel holes having a diameter of 1 mm with a pitch of 1.5 mm and provided in an aluminium block having a thickness of from some tenths of a mm to a few mm, and which covers the entire field of view of 30 by 40 mm. This collimator may also be made of brass or of copper in a thickness of some tenths of a min. The modulating grid 312 for the β radiation is preferably formed by a copper or brass sheet having a thickness of typically 0.5 mm, which sheet is provided with holes having a diameter of 1 mm and a pitch of 1.5 mm, the sheet being driven in a vibratory fashion at a frequency of between some hundredths of Hz and some Hz, so that the holes of the collimator are sequentially obturated by the solid parts of the grid. In the scintillator 302 the electrons β which form an energetic continuum interact and loose all or part of their energy. A preferred embodiment of the scintillator consists of a thin sheet having a thickness of between 0.5 and 1.5 mm and being made of a plastic material of the type NE 102 or NE 108. The device 309 for reading images in accordance with the invention utilizes the properties of the matrix 304 in a special manner so as to improve the signal-to-noise ratios, taking into account the spatial resolution characteristics of the β and γ minicamera itself, preferably in the output mode with macropixels (patterns of p×q pixels) at a reduced image frequency, i.e. of the order of 4 or 5 matrix images per second. This operation can be obtained simply by means of a Peltier refrigerator which keeps the charge transfer detector matrix at a temperature of the order of 5° C. and, if necessary, at a lower temperature, of even −40° C. By adequate sequencing of the reading of the matrix, synchronized with that of the positioning of the modulating grid 312, these matrix images are applied either to the first memory 423 (with open grid) or to the second memory 424 (with obturating grid). The number of matrix images to be applied to the memories 423 and 424 in a fixed position of the image pick-up head may vary from several tens to several thousands of images, the measuring time thus varying from a few seconds to some tens of minutes. Steps can be taken to ensure that the same number of images, of equal integration time over the matrix, is stored in the memories 423 and 424. Thus, the γ signal detected is substantially the same in each of the two memories, considering that the collimator 301 as well as the grid 312 is transparent to the γ radiation. However, this is only true in a first approximation, because a slight bias in the nature and the quantity of the γ radiation, due to the induction of a slight Comton effect through the collimator and the grid, is introduced by the different relative positions of these two elements. This bias can be measured by prior calibration of a pure γ emission corrected by any means known to those skilled in the art, for example by making the positioning times of the grid in the open and obturating position slightly different.

The detected β radiation signal is obtained only with an open grid and is added to the γ signal in the memory 424. The useful images for display are obtained by simple difference, pixel by pixel, between the contents of the two memories, said images being stored, for example in a third memory 425.

It is to be noted that the above bias can also be corrected by application of a suitable multiplication coefficient to the signals in one in the memories 423 or 424 in order to equalize the γ signals. More generally speaking, an alternative version of this embodiment of the invention consists in making the positioning times of the grid in the open position preponderant relative to those in the obturating position. This enables an increase of the number of β detected and hence an increase of the useful signal. An inversely proportional weighting operation is subsequently performed by the means for calculation and comparison which form the processor 421, which operation is combined with a weighting operation to eliminate said bias introduced in the γ signal; subsequently, the γ signal can be eliminated by subtraction and the result can be applied to the memory 425.

Figure 2:
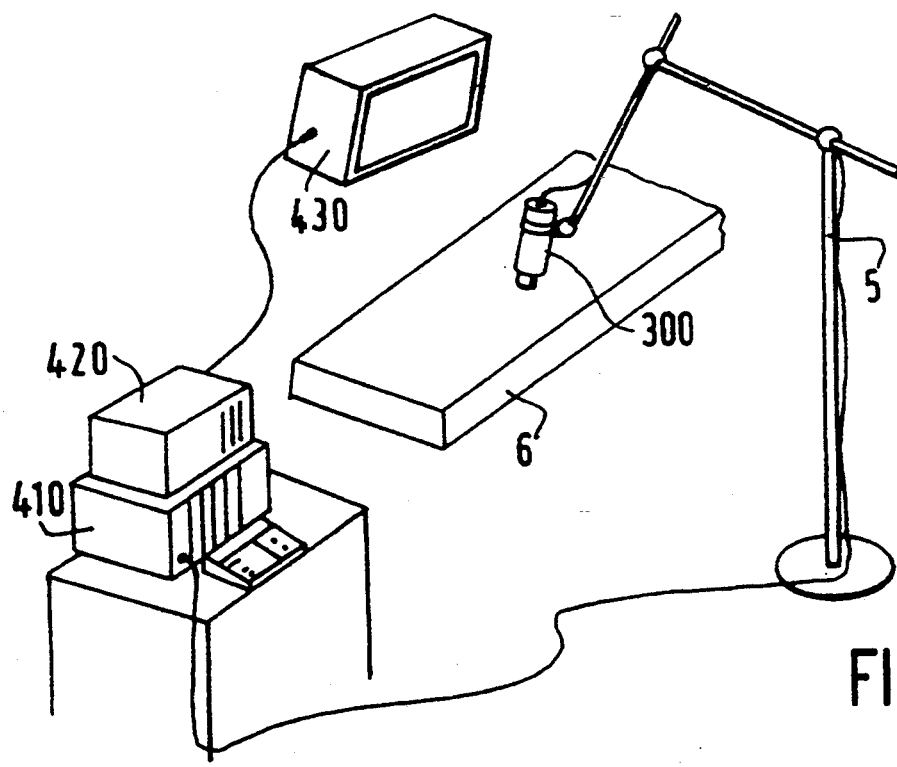
FIG. 2 is a perspective front view of the assembly enabling application of the minicamera in accordance with the invention in a surgical system.

FIG. 2 shows the installation of a minicamera in accordance with the invention in an operating room. The image pick-up head 300 is secured to a technical positioning means, for example a stand 5 comprising balanced arms, similar to those used for ultrasonic medical apparatus, thus enabling the displacement of the head over an operating table 6. FIG. 2 also shows the electronic unit 410, the imaging sub-assembly 420 and the television monitor 430.

The described equipment is preferably designed to utilize the useful images (stored in the memory 425), including storage, accumulation, and rereading with the TV standard, and to perform image processing operations such as contour searching, representation in false colours and false perspectives currently used in medical imaging, thus enabling further enhancement of the coarse useful image stored in the memory 425 and hence facilitating their interpretation.

Figure 3:
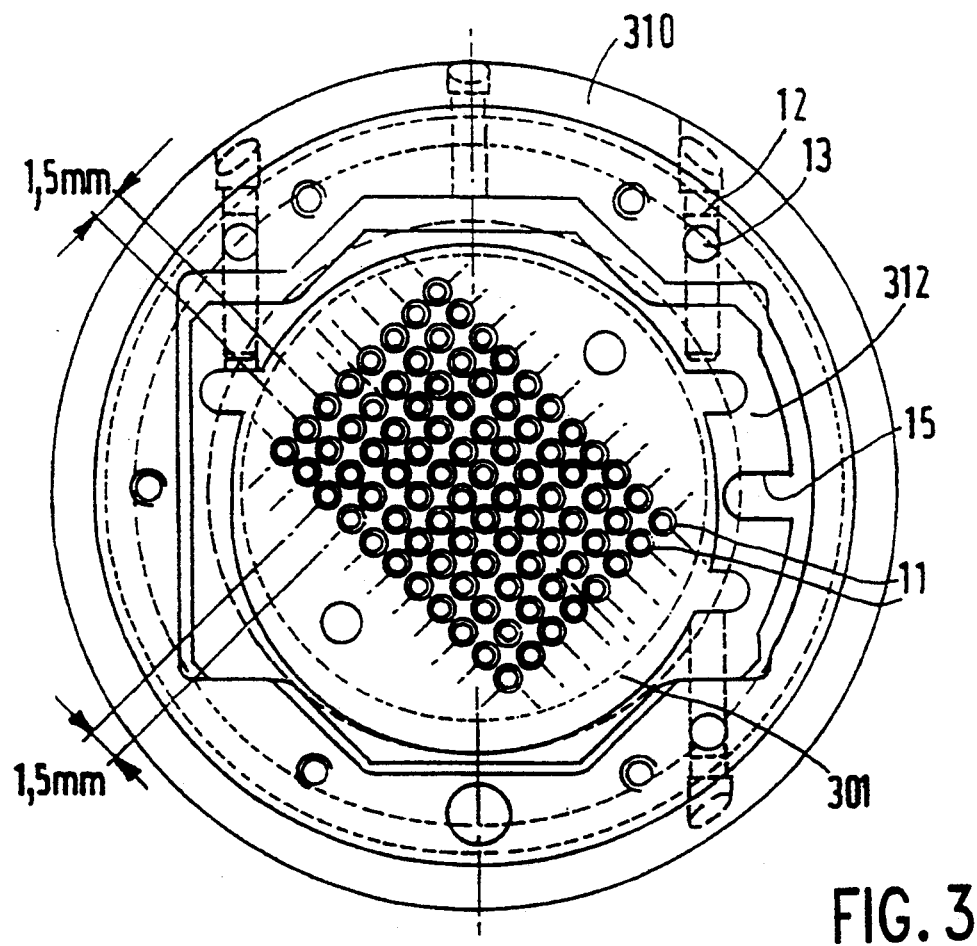
FIG. 3 is a bottom view of given parts of the front section of an image pick-up head of the minicamera in accordance with the invention.

Example of an embodiment of the image pick-up head of a β and γ for operations:

the dimensions of the field of vision are: 12 mm×16 mm as shown in FIG. 3. the β radiation collimator 301, comprising parallel holes 11 (diameter 1 mm and pitch 1.5 mm) is constructed so as to comprise two sections:

a fixed section which is made of aluminium and has a thickness of 1 mm, and a mobile section which is also made of aluminium, has a thickness of 1 mm, and is mechanically connected to the copper modulating grid 312 having a thickness of 0.3 mm.

The sub-assembly formed by the collimator and the modulating grid covers the field of vision, having a diameter of 20 mm, and has an overall height amounting to 3 mm.

The modulating grid is translatable and mounted so as to be slidable by means of three slotted holes 12 which are traversed by three pins, such as 13, which are integral with the casing 310. A lever, denoted by the reference 14 in FIG. 4, engages in a groove 15 of the grid and causes the desired alternating translatory movement. To this end, the lever 14 is rotated sectorially by a shaft 15 which itself is driven by an electric motor 16 which rotates a cam 17.

Figure 4:
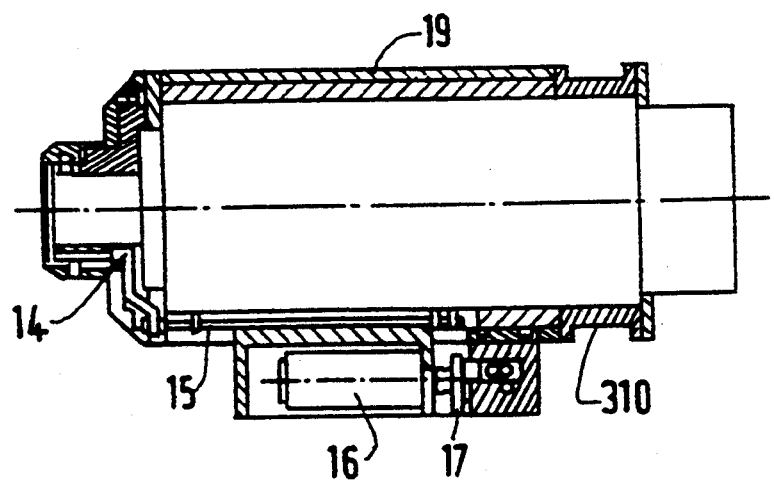
FIG. 4 is a cross-sectional view of a casing for the image pick-up head shown in FIG. 3.

The plastics scintillator, not shown in the FIGS. 3 and 4, is a disc of a plastics material of the type NE 102 or NE 108 which has a thickness of from 0.5 to 1 mm and a diameter of 20 mm. It is coupled directly to a non-reducing bundle of optical fibres, having a diameter of 20 mm and a length of 30 mm, which provides the image transfer to the photocathode of the image intensifier tube. The image pick-up head is designed to accommodate two types of image intensifier tube with fibre-optical entrance and exit windows: either a first-generation image intensifier tube, for example of the Philips type DEP XX1490, or a so-called second-generation image intensifier tube, for example of the Philips type DEP XX1410 which is shorter than the first-generation image intensifier tube. The circuit DTC is a matrix TH 7863 manufactured by Thomson and cooled to 5° C. by the Peltier effect, said matrix being coupled either directly to the exit window of the first-.generation image intensifier tube, or to the exit window of the second generation image intensifier tube by means of a reducing bundle of optical fibres.

Preferably, the mechanical construction of the image pick-up head is split into two independent structural parts, one (internal) part allowing for the mechanical positioning of the optical fibre bundles of the image intensifier tube, the cooled matrix and the electronic read circuitry, whereas the other part (shown in FIG. 4) is concentric with and external of the former part and comprises the lead shield 19 having a thickness of 5 mm and allows for the mechanical positioning of the assembly formed by the collimator and the modulating grid, and also supports the already described translation mechanism which is formed by the reducer micromotor 16 associated with the cam 17 and the actuating system 14., 15. The positions of the cam 17 are picked up by two photocouplers in order to enable synchronization of the mechanical movement with the sequencing of the reading of the matrix.

The electronic circuitry 400 of the $\beta$ and $\gamma$ minicamera can be as described above.

A minicamera actually resembling those described above for composite $\beta$ and $\gamma 0$ radiation can be conceived and used, in accordance with the invention, for the detection and imaging of $\gamma$ radiation associated with conversion electrons.

For the two embodiments of the invention as described above, i.e. $\beta$ and $\gamma$ minicamera and $\gamma$ minicamera with conversion electrons, the preferred field of application is that of assisting surgeons in localizing lesions where they must perform the excision without removing healthy tissues.

Other types of application can be envisioned, after making some structural adaptations, by those skilled in the art, notably:

applications involving autoradiography of removed tissues and cellular cultures marked either by pure $\beta$ emitting isotopes (such as $^{32}p$, $^{89}Sr$, $^{36}Cl$ ... ) or by $\beta$ and $\gamma$ emitting isotopes (such as $^{131}I$) in the field of biology and immunology;

applications aiming to establish a functional diagnosis of given organs, marked in advance, by means complementary to those used in nuclear medicine (examinations of the thyroid, of accessible regions of the eyeball, of glands situated near the cutaneous surface, cutaneous melanomata ... );

applications aiming to map superficial regions activated subsequent to nuclear interactions caused by particle beams, for example in the field of neutron analysis or in the field of surface treatment by ion or electron beams.

The industrial applications concern the visualization of the surface emission of marked objects activated or polluted by $\beta$ and $\gamma$ emitters or $\gamma$ emitters with conversion electrons such as $^{137}Cs-^{137m}Ba$ or $^{133}Sn-^{113m}In$.

We claim:

1. A minicamera for the detection of at least a composite $\beta$ and $\gamma$ nuclear radiation, or a $\gamma$ nuclear radiation associated with conversion electrons assimilated with a $\beta$ radiation, emitted by a radioisotope present in a body, said minicamera having an image pick-up head comprising a $\beta$ radiation collimator which is transparent to the $\gamma$ radiation, a scintillator and a photodetector assembly, characterized in that said image pick-up head also comprises a modulating grid with holes which is arranged between the collimator and the scintillator so as to be movable by a mechanism so that in an alternating fashion it opens the holes of the collimator in a first position and closes these holes in a second position, said photodetector assembly being controlled so as to integrate the alternating signals supplied by the scintillator in said first position and said second position of the modulating grid and to apply these signals selectively to a first, open-grid image memory and to a second, closed-grid image memory, said minicamera also comprising means for calculation and comparison of signals stored in said first and second image memories in order to supply the useful image to be displayed.

2. A minicamera as claimed in claim 1, characterized in that said image pick-up head also comprises an external protective diaphragm.

3. A minicamera for the detection of nuclear radiation emitted by a radioisotope as claimed in claim 1 in which the collimator, intended for the $\beta$ radiation is transparent to the $\gamma$ radiation, characterized in that the solid part of said modulating grid is transparent to the $\gamma$ radiation but opaque to the $\beta$ radiation, and that said means for calculation and comparison are conceived so as to weight the signals of the first and the second memory in order to achieve equal signal integration times for correction of the bias introduced on the $\gamma$ signal by the changing of the position of the grid, and subsequently to take as the useful image signal to be displayed the difference between the contents of the homologous pixels, weighted and corrected for their bias, of the first image memory and the second image memory.

4. A minicamera for the detection of a composite $\beta$ and $\gamma$ nuclear radiation as claimed in claim 3 in which said photodetector assembly comprises a charge transfer detector matrix which is at a temperature of between $-40°$ C. and $5°$ C. and which operates at a frequency of between 0.01 Hz and a few Hz, characterized in that the alternating periods of opening and closing of the modulating grid are equal and have a duration of between a few seconds and some tenths of a second, and that in said first and second image memories from several tens to several thousands of images of said charge transfer detector matrix are added by said calculation and comparison means, after which the contents of the second image memory is pixel-wise subtracted, after correction for said bias, from the contents of the first image memory in order to supply the pixels of the useful image to be displayed.

5. A minicamera for the detection of a composite $\beta$ and $\gamma$ radiation as claimed in claim 3 said radiation being emitted by $^{131}I$, and comprising an external protective diaphragm which is made of metallized Kapton or vinyl, is opaque to visible radiation, and has a thickness of from some tens to some hundreds of microns, a collimator which comprises parallel holes with a diameter of 1 mm and a pitch of 1.5 mm, is made of aluminium or brass, and has a thickness of from some tenths of a mm to a few ram, a modulating grid which is made of aluminium, copper or brass, has a thickness of some tenths of a mm and is pierced like said modulator, and a scintillator which is formed by a sheet of a plastics material of the type NE 102 or 108, has a thickness of between 0.5 and 1.5 mm and covers the field of view of the order of a few cm$^2$.

6. A minicamera for the detection of nuclear radiation emitted by a radioisotope as claimed in claim 2 in which the collimator, intended for the $\beta$ radiation is transparent to the $\gamma$ radiation, characterized in that the solid part of said modulating grid is transparent to the $\gamma$ radiation but opaque to the $\beta$ radiations, and that said means for calculation and comparison are conceived so as to weight the signals of the first and the second memory in order to achieve equal signal integration times for correction of the bias introduced on the $\gamma$ signal by the changing of the position of the grid, and subsequently to take as the useful image signal to be displayed the difference between the contents of the homologous pixels, weighted and corrected for their bias, of the first image memory and the second image memory.

7. A minicamera for the detection of a composite $\beta$ and $\gamma$ nuclear radiation as claimed in claim 6 in which said photodetector assembly comprises a charge transfer detector matrix which is at a temperature of between −40° C. and 5° C. and which operates at a frequency of between 0.01 Hz and a few Hz, characterized in that the alternating periods of opening and closing of the modulating grid are equal and have a duration of between a few seconds and some tenths of a second, and that in said first and second image memories from several tens to several thousands of images of said charge transfer detector matrix are added by said calculation and comparison means, after which the contents of the second image memory is pixel-wise subtracted, after correction for said bias, from the contents of the first image memory in order to supply the pixels of the useful image to be displayed.

8. A minicamera for the detection of a composite $\beta$ and $\gamma$ radiation as claimed in claim 6, said radiation being emitted by $^{131}$I, and comprising an external protective diaphragm which is made of metallized Kapton or vinyl, is opaque to visible radiation, and has a thickness of from some tens to some hundreds of microns, a collimator which comprises parallel holes with a diameter of 1 mm and a pitch of 1.5 mm, is made of aluminum or brass, and has a thickness of from some tenths of a mm to a few mm, a modulating grid which is made of aluminum, copper or brass, has a thickness of some tenths of a mm and is pierced like said modulator, and a scintillator which is formed by a sheet of a plastics material of the type NE 102 or 108, has a thickness of between 0.5 and 1.5 mm and covers the field of view of the order of a few cm$^2$.

9. A minicamera for the detection of a composite $\beta$ and $\gamma$ radiation as claimed in claim 4, said radiation being emitted by $^{131}$I, and comprising an external protective diaphragm which is made of metallized Kapton or vinyl, is opaque to visible radiation, and has a thickness of from some tens to some hundreds of microns, a collimator which comprises parallel holes with a diameter of 1 mm and a pitch of 1.5 mm, is made of aluminum or brass, and has a thickness of from some tenths of a mm to a few mm, a modulating grid which is made of aluminum, copper or brass, has a thickness of some tenths of a mm and is pierced like said modulator, and a scintillator which is formed by a sheet of a plastics material of the type NE 102 or 108, has a thickness of between 0.5 and 1.5 mm and covers the field of view of the order of a few cm$^2$.

10. A minicamera for the detection of a composite $\beta$ and $\gamma$ radiation as claimed in claim 7, said radiation being emitted by $^{131}$I, and comprising an external protective diaphragm which is made of metallized Kapton or vinyl, is opaque to visible radiation, and has a thickness of from some tens to some hundreds of microns, a collimator which comprises parallel holes with a diameter of 1 mm and a pitch of 1.5 mm, is made of aluminum or brass, and has a thickness of from some tenths of a mm to a few mm, a modulating grid which is made of aluminum, copper or brass, has a thickness of some tenths of a mm and is pierced like said modulator, and a scintillator which is formed by a sheet of a plastics material of the type NE 102 or 108, has a thickness of between 0.5 and 1.5 mm and covers the field of view of the order of a few cm$^2$.

11. A method of using a minicamera in conjunction with excision of a tumor from an organism, said minicamera being configured for detection of one of composite $\beta$ and $\gamma$ nuclear radiation emitted by a tracer radioisotope present in the organism, said minicamera having an image pick-up head comprising a radiation collimator for the one of composite $\beta$ and $\gamma$ to be detected which is transparent to the other of composite $\beta$ and $\gamma$ radiation, a scintillator and a photodetector assembly, which image pick-up head also comprises a modulating grid with holes which is arranged between the collimator and the scintillator so as to be movable between first and second positions so that it opens the holes of the collimator in the first position and closes these holes in a second position, comprising the steps of moving the modulating grid alternately between the first and second positions, integrating signals alternately supplied by the scintillator in said first and second positions of the modulating grid, calculating and comparing signals the integrated signals alternately supplied in the first and second position of the modulating grid to generate a useful image to be displayed, and applying said image pick-up head against an incision made in said organism in the course of surgery in alternation with phases of excision of the tumor.

* * * * *